United States Patent
Baumgartner (10) Patent No.: US 10,842,544 B2
(45) Date of Patent: Nov. 24, 2020

(54) DEVICE FOR FIXATING A KIRSCHNER WIRE

(71) Applicant: Heiko Baumgartner, Tuebingen (DE)

(72) Inventor: Heiko Baumgartner, Tuebingen (DE)

( * ) Notice: Subject to any disclaimer, the term of this patent is extended or adjusted under 35 U.S.C. 154(b) by 379 days.

(21) Appl. No.: 15/310,007

(22) PCT Filed: May 11, 2015

(86) PCT No.: PCT/EP2015/000968
§ 371 (c)(1),
(2) Date: Nov. 9, 2016

(87) PCT Pub. No.: WO2015/169453
PCT Pub. Date: Nov. 12, 2015

(65) Prior Publication Data
US 2017/0135738 A1 May 18, 2017

(30) Foreign Application Priority Data
May 9, 2014 (DE) .................... 20 2014 003 940 U (51) Int. Cl.
*A61B 17/84* (2006.01)
*A61B 17/86* (2006.01)
(Continued)

(52) U.S. Cl.
CPC ............ *A61B 17/84* (2013.01); *A61B 17/842* (2013.01); *A61B 17/848* (2013.01);
(Continued)

(58) Field of Classification Search
CPC ..... A61B 17/84; A61B 17/842; A61B 17/848; A61B 17/8695; A61B 17/82;
(Continued)

(56) References Cited

U.S. PATENT DOCUMENTS 5,209,756 A * 5/1993 Seedhom ........... A61B 17/0642
606/151
5,306,301 A * 4/1994 Graf .................... A61B 17/0401
606/151
(Continued)

FOREIGN PATENT DOCUMENTS

DE  10 2012 004 070 A1  9/2013
EP       0 298 400 A1    1/1989
(Continued)

OTHER PUBLICATIONS

"K-Wire Sizes." Kirschner Wires, Jun. 13, 2013, www.kirschnerwires.com/k-wire-sizes/. Accessed on Jun. 19, 2019. (Year: 2013).*

*Primary Examiner* — David W Bates
*Assistant Examiner* — Marcela I Shirsat
(74) *Attorney, Agent, or Firm* — Muncy, Geissler, Olds & Lowe, P.C.

(57) ABSTRACT

The invention relates to a fixating device composed of plastic or metal for medical care, which fixating device interacts with a Kirschner wire (9) as a fastening means, comprising an opening for accommodating the fastening means and at least two further openings for accommodating fastening material in the form of stitches (13) and wires. The Kirschner wire (9) reaches through the one opening and is retained in the one opening in a positionally stable manner by the fastening material. The fixating device can be designed as a plate (101), be domed on all sides (1), or be designed as a sphere segment (211). The invention further relates to the use of the fixating device for osteosynthesis.

17 Claims, 7 Drawing Sheets

(51) Int. Cl.
*A61B 17/064* (2006.01)
*A61B 17/04* (2006.01)

(52) U.S. Cl.
CPC ....... *A61B 17/0401* (2013.01); *A61B 17/0642* (2013.01); *A61B 17/0643* (2013.01); *A61B 17/8695* (2013.01); *A61B 2017/0641* (2013.01)

(58) Field of Classification Search
CPC ... A61B 17/846; A61B 17/86; A61B 17/8645; A61B 17/0642; A61B 17/0401; A61B 17/0643; A61B 2017/0641
USPC .................................. 606/300, 268, 263, 74
See application file for complete search history.

(56) References Cited

U.S. PATENT DOCUMENTS

| | | | |
|---|---|---|---|
| 5,800,436 A | | 9/1998 | Lerch et al. |
| 6,117,139 A | * | 9/2000 | Shino ................ A61B 17/0401 606/300 |
| 2004/0073222 A1 | * | 4/2004 | Koseki ............... A61B 17/0642 606/75 |
| 2010/0069969 A1 | | 3/2010 | Ampuero et al. |
| 2011/0029025 A1 | | 2/2011 | Medoff |
| 2011/0213422 A1 | * | 9/2011 | Gannoe ................ A61B 17/683 606/300 |

FOREIGN PATENT DOCUMENTS

| | | |
|---|---|---|
| FR | 2 703 239 A1 | 10/1994 |
| FR | 2 921 246 A1 | 3/2009 |

\* cited by examiner

PRIOR ART

DEVICE FOR FIXATING A KIRSCHNER WIRE

This application is a national stage of International Application No.: PCT/EP2015/000968, which was filed on May 11, 2015, and which claims priority to German Patent Application No.: 20 2014 003 940.2, which was filed in Germany on May 9, 2014, and which are both herein incorporated by reference.

The present invention relates to a fixating device for Kirschner wires for the medical supply in surgery, in order to prevent their wandering or loosening, such as in the case of tension band wiring during osteosynthesis.

The basic medical goal for every bone fracture is that the bone grows together quickly in a functional position. This cannot always be achieved by longer immobilization using a plaster cast, but rather, an operative procedure is required in order to reassemble the bones or fractures. For this purpose, the broken ends are joined in the correct position, in order to fixate them in the respective position by means of nails, screws, plates or special wires.

The special wires mentioned are referred to as Kirschner wires, named after their inventor. Such a Kirschner wire is a pointed wire, with or without a thread, made of steel, a nickel-containing metal alloy, or titanium. The Kirschner wire is drilled into the bone by rotation. While it was originally used only for attaching an extension, later, osteosynthesis (bone fusion) was added within the scope of fracture treatment and has proven itself, so that the Kirschner wire still serves today for the closed reduction and fixating of bone fractures. Kirschner wires can be bent at the bone or sunk into it, or inserted percutaneously.

In order to connect broken bones, Kirschner wires are also laid around the bones, which is referred to as tension band wiring. The principle of tension band wiring is based on the fact that a tensile-resistant structure, which is abarticularly fixed as much as possible, bears against the fracture fragments in the form of a wire loop, and is arranged around the tendon or bone extensions. As a result of the active movement, in particular flexion, the tensile stress acting against the wire loop is converted into a compressive stress in the fracture gap so that the fragments can approach and compress each other. Thus, they are held together in a correct position by the tension band, and the fracture gap is healed.

Traditionally, this type of osteosynthesis was the ideal medical treatment for the olecranon and the patella. Even today, it is the standard form of care at these points, but also in other areas. Worth mentioning are the great trochanter of the femur or of the humeral head, the inner ankle bone, the base of the fifth metatarsal, the radial styloid process, the distal part of the clavicle, even the acromion, or the intermittent immobilization of the acromioclavicular joint.

Advantages of osteosynthesis using Kirschner wires are, in principle, a low operating expense and a low degree of invasiveness.

However, disadvantages are also known. Since the Kirschner wire is very flexible, the result of the operation is usually not stable to movement. Complications mentioned are migration of the wires and/or wire breakage. The possible complications are described in more detail below.

Numerous publications reveal a problem in the design of the above-described tension band. In the literature, up to 80% of complications are indicated in connection with osteosynthesis caused by tension band wiring.

For one, the tensioning can loosen if, for example, the straight drill wires gain a bad hold, if they are not bicortically inserted or are loosened by too little pull of the wire loop. In these cases, there may be a return travel of the wire. As a result, the stability at the height of the fracture gap is considerably reduced. There is a tilting of the fragments, an enlargement of the fracture gap and ultimately pseudoarthrosis, or even a complete failure of the construction, leading to a dehiscence of the fragments with loss of function of the stretching apparatus.

Secondly, the bent part of the drill wires protruding from the bone can rotate by more than 90°, whereby the wire loop slides over the straight wires and thus also causes a failure of the construction. As a result, an increased rate of premature joint wear will ultimately occur.

Furthermore, in places with only a small amount of soft tissue cover (for example, in the case of the olecranon), there is the problem of the protruding, bent, wire-loop-fixating, Kirschner wire. Even if its position is correct, said wire can cause a maximum acting, punctiform pressure from subcutaneous to cutaneous, which can cause physically defined soft tissue damage, by for example regular leaning, a one-time bump of the elbow, or even just because of the thin skin/subcutaneous covering. This, in turn, regularly leads to open wounds, resulting in implant-associated infections with early material removal and dissolution of osteosynthesis. In particular, pain caused by protruding Kirschner wires, by the metal as a whole or also by palpable drill wires, are the main reason for a necessary second operation, to remove the metal.

In order to prevent loosening of the drill wires, for example in the patella tensioning, both ends of the Kirschner wires are often bent over. During metal removal, however, this means that the drill wire has to be approached from both ends so it can be removed. Two access points must therefore be created, which in turn can lead to additional disruptions to wound healing, and to more pain.

At this time, there is no device which satisfactorily resolves the above-described problems. In particular, there is no device which simultaneously prevents all the described complications. Only the company Acumed® introduced a Tension Band Pin in December 2010, in which the drill wire makes a firm connection with the tension band wire ("Complications and re-operation rate after tension-band wiring of olecranon fractures," Romero J M, Miran A, Jensen; CH, J Orthop Sci. 2000; 5(4):318-20). For the first time, this principle was previously described by P. Netz and L. Stromberg in 1982 (Netz P. and Stromberg L. 1982. "Non-Sliding pins in traction absorbing wiring of fractures" Acta Orthop Scand, 53:355-360).

Based on this, it is the object of the present invention to provide a fixating device for the medical supply, which makes it possible to fixate fastening means used in surgery, in particular Kirschner wires, preventing both a loosening and migration of the wire, while at the same time providing a soft-tissue protective cover for the wire.

This object is achieved by means of a fixating device for the medical supply which cooperates with at least one fastening means and which has at least one opening for receiving the fastening means, which passes through the at least one opening, and is retained in a positionally stable manner in the latter by a fastening material.

Preferably, the fixating device according to the invention is designed planar as a plate, domed on all sides or cap-shaped as a sphere segment.

In addition, the diameter of the opening can be made smaller than the maximum extent of the fastening means penetrating the opening transversely to the penetration direction.

In this way it can be ensured that the fastening means projects only partially through the longitudinal hole. It is not completely passed through the longitudinal hole and does not slide through it but is retained by it and in it.

According to a preferred embodiment of the inventive fixating device, the opening is designed as a longitudinal hole, as a round hole, ellipsoid, oval or rectangular in cross-section, wherein the design of the opening is a combination of the forms mentioned.

It can also be provided that the fixating device according to the invention has, in addition to the one opening, at least two further openings for receiving the fastening material.

According to a further preferred embodiment, the fixating device can have an enlarged head region, to which a tapering is adjoined.

In a further development of the fixating device according to the present invention, the opening can be formed as a longitudinal hole, wherein the longitudinal hole has at least one bulge on both sides along its longitudinal direction, and these bulges are formed in a regular or irregular manner with respect to the longitudinal hole.

The fixating device according to the present invention can be designed as a sphere segment, wherein recesses are formed peripherally distributed on its outer boundary.

Furthermore, it can be provided that the fixating device according to the invention is formed as an annular oval, which in its interior forms an opening designed as an oval longitudinal hole, wherein tunnel-like elevations are arranged opposite one another and cooperating with each other.

The fastening means engaging through the opening may be designed as a Kirschner wire.

According to yet another preferred embodiment of the fixating device according to the invention, the opening is designed as a longitudinal hole and the fastening means engaging through the opening is designed as a Kirschner wire, the longitudinal and transverse diameters of the longitudinal hole being tailored to the thickness of the Kirschner wire.

For this purpose, the transverse diameter of the longitudinal hole can be designed such that it corresponds to the diameter of the Kirschner wire used, plus at least 0.05 mm, preferably plus 0.1 mm, and not exceeding plus 1.0 mm.

The fastening material may be stitches and wires.

Preferably, the fixating device according to the invention is made of plastic or metal and the metal is selected from stainless steel or titanium.

The invention also relates to the use of the fixating device in one of its aforementioned embodiments within the context of osteosynthesis.

The advantages achieved by the invention presented here, if appropriate, designed as one of its particular configurations, which have also been mentioned, and in the context of their preferred use, are now presented as a whole.

Through the use of the fixating device according to the invention, firm retention of a drilling wire that is used for osteosynthesis is achieved so that its backward wandering and twisting is prevented. The fixating device according to the invention makes it possible that no additional anchoring is necessary in the surrounding soft tissue or bony structures. In addition, the maximum load on the soft tissue lying above the bone fracture area is reduced by increasing the surface. It is important that the use of the fixating device according to the invention makes it unnecessary to bend over the drill wires at the two ends, as is the case, for example, when tensioning a patella fracture.

Overall, the fixating device represents a cost-effective and, at the same time, simple way of reducing the complication rate in tension band wiring.

Furthermore, the fixating device according to the invention provides a sensible and cost-effective extension for devices in which expensive angularly stable plates cannot be used, and effective tensioning can also be performed on an osteoporotic bone.

It is particularly noteworthy that the fixating device according to the invention is applied only after completion of the construction required for osteosynthesis, and that a predetermined length of the drill wires need not be used.

The invention will now be described in more detail by means of exemplary embodiments in conjunction with the appended drawings. The drawings show.

EXEMPLARY EMBODIMENT I.1

Figure 1A:
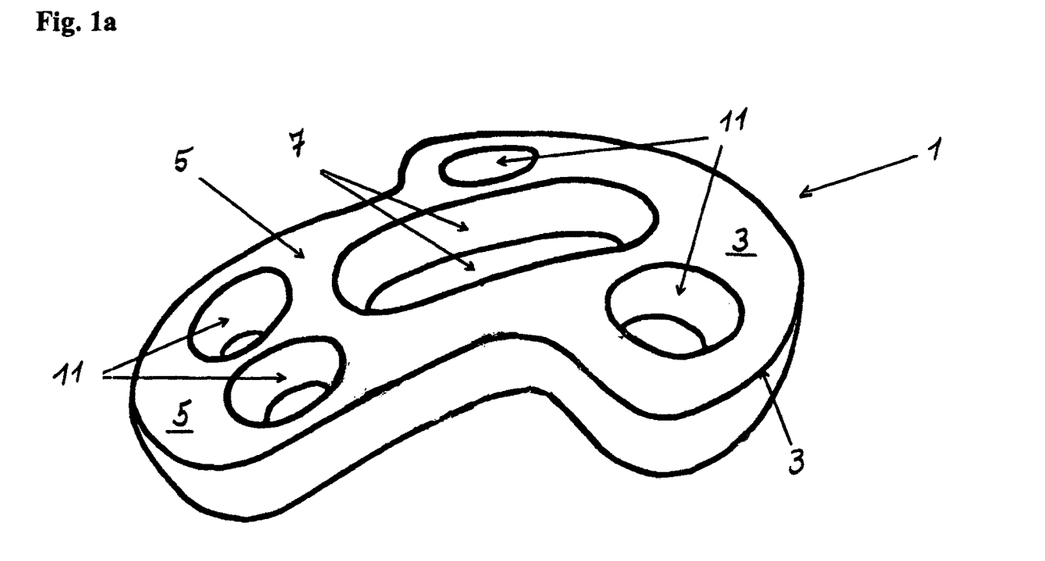
FIG. 1*a*: a three-dimensional view of a fixating device according to the invention, domed on all sides, according to a first exemplary embodiment.
Figure 1B:
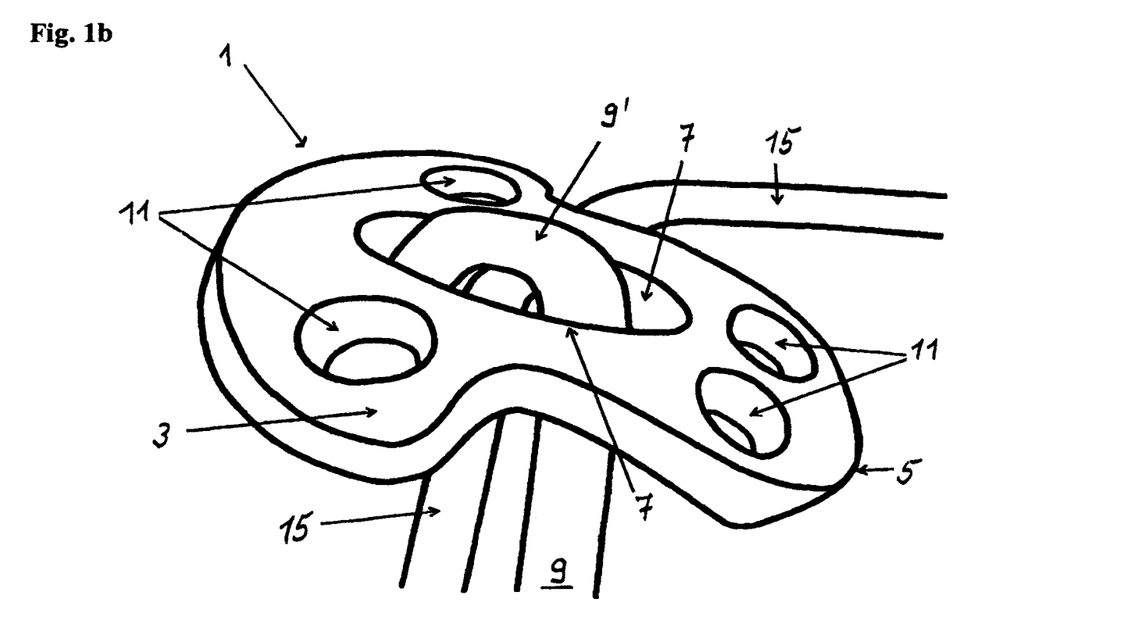
FIG. 1*b*: a three-dimensional view of the fixating device according to FIG. 1*a* in conjunction with osteosynthesis by tensioning, without accompanying fastening material.
Figure 1C:
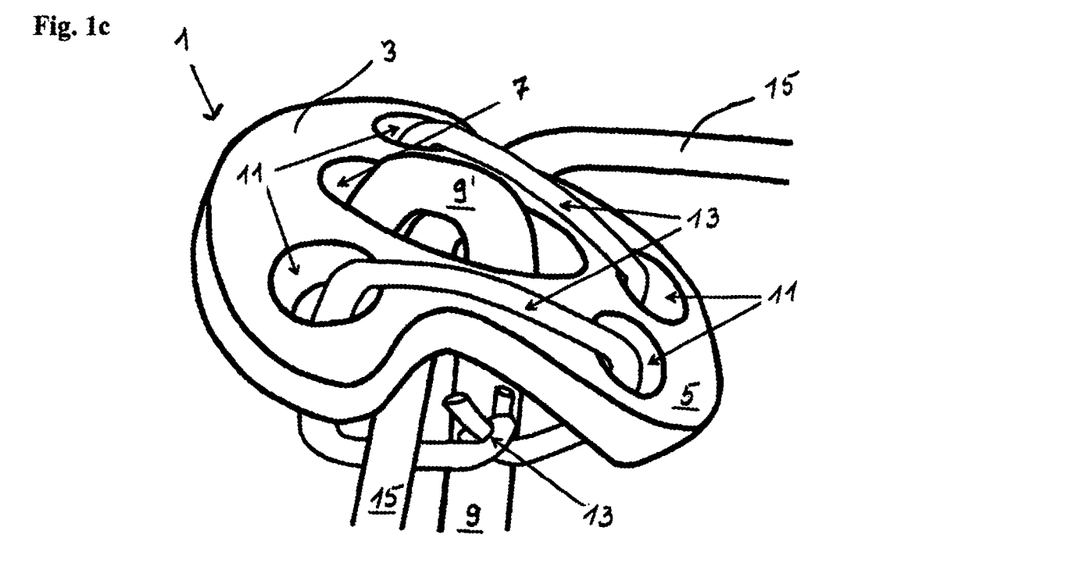
FIG. 1*c*: a three-dimensional view of a fixating device according to FIG. 1*b*, with accompanying fastening material.

Fixating Device with all-Round Domed Design:

A first embodiment of the fixating device according to the invention is shown in FIG. 1a and is denoted overall by the reference numeral 1. The fixating device 1 according to this exemplary embodiment is flattened in plan and is approximately mushroom-shaped so that it has an enlarged head region 3, which is adjoined by a tapering 5. Approximately centrally, the fixating device 1 has an opening designed as a longitudinal hole 7 which extends in the longitudinal direction thereof in the direction of the tapering 5 of the fixating device 1 and whose narrow sides are closed by half circles, whose diameter corresponds to the width of the longitudinal hole 7. This longitudinal hole 7 serves to receive the bent-over part of a fastening means in the form of a drill or Kirschner wire 9, as shown in FIGS. 1b and 1c, wherein the bent part of the Kirschner wire 9 is additionally provided with the reference numeral 9' for the sake of better clarity. As can be seen from FIGS. 1b and 1c, the bent-over part 9' of the drill wire or Kirschner wire 9 passes through the longitudinal hole 7.

Correspondingly, the longitudinal and transverse diameters of the longitudinal hole 7 are aligned and matched to the thickness of the Kirschner wire 9 used. The longitudinal and transverse diameters of the longitudinal hole 7 can thus vary as a function of the strength of the Kirschner wire 9 to be used. In principle, the transverse diameter of the longitudinal hole 7 is designed such that it corresponds to the diameter of the Kirschner wire 9 used, plus at least 0.05 mm, preferably plus 0.1 mm, and maximally plus 1.0 mm.

With respect to the diameter of the longitudinal hole 7 in its longitudinal direction, it is important that this longitudinal diameter is smaller than the maximum extent of the bent portion of the Kirschner wire 9 extending through the longitudinal hole 7 in this longitudinal direction.

In this way, it is ensured that the Kirschner wire or drill wire 9 extends only partially through the longitudinal hole 7, as shown in FIGS. 1b and 1c by way of illustration. However, it cannot be completely passed through the longitudinal hole 7, i.e., slip through it, but rather is retained by it and in it.

The fact that the two limbs of the bent Kirschner wire or drill wire 9 are closer to one another in the region of the bending and thus are spaced apart from one another less than in the further course of the bending is hereby put to use.

The fact that the Kirschner wire or drill wire 9 extends only partially through the longitudinal hole 7 and cannot slip through the longitudinal hole 7, but rather is retained in the latter, represents a fundamental feature of the fixating device according to the invention, which is also decisive for the following exemplary embodiments and their variants, even without this being explicitly mentioned again.

For those skilled in the art, it is readily apparent from the illustrated purpose of the longitudinal hole 7 to receive the bent portion of the Kirschner wire 9, that the receptacle of the Kirschner wire 9 is not limited to the longitudinal hole 7 shown for the purpose of illustrating the invention. Instead of the longitudinal hole 7, the opening for the Kirschner wire 9 may, for example, also be ellipsoid, oval or rectangular in cross-section, and may include a combination of these shapes. This list is not intended to be exhaustive.

In the exemplary embodiment described here, in each case adjacent to the two ends, in the longitudinal direction of the longitudinal hole 7, are two further openings designed as holes 11, which are circular. These are used to receive fastening material. Stitches and wires are to be mentioned in particular, among them polyethylene specialty yarns made from UHMWPE, commercially available from Arthrex, Inc. under the brand name FiberWire®. Thus, for example, stitches 13 are introduced here and, with the inclusion of a cerclage wire 15 attached to the fracture, knotted between said wire and the bone, which is illustrated in FIG. 1c. Cerclage, in principle, is understood in medical terms to be a wire looping which is known, for example, as a looping used in patella fractures or with the olecranon.

The guidance of the cerclage wire 15 is also already apparent from FIG. 1b and shows that the bent part of the Kirschner wire 9 grips the cerclage wire 15. In this exemplary embodiment, the further holes 11 have a diameter of at least 0.6 mm in order to be able to incorporate a strong fastening material.

The fixating device 1 is domed on all sides. In this case, the surface facing away from (distally located from bone or body) the imaginary bone or body which is to be fixated is convex, and the surface (proximate to bone or body) facing this bone or body is concave. Due to this all-round domed design, a significant improvement in the pressure conditions is achieved in the sense that the pressure for the overlying soft tissue is significantly reduced by an increase in the surface.

Suitable material for the illustrated fixating device 1 is not only metal, here preferably titanium, but also plastic. All the edges of the respective openings of the fixating device, i.e. of the longitudinal hole 7 as well as of the additional circularly formed holes 11 are deburred in the exemplary embodiment. The same applies to the external edges of the fixating device.

When Kirschner drill wire 9 alone is used, i.e., without the use of the cerclage 15, the fixating can be performed transosseously by means of a bone suture. The standalone wire or wires 9 are then secured to the bone or soft tissue with fastening material by means of the fixating device 1. The described fixating device 1 according to the invention can be used in so-called spike wire osteosynthesis. In this fixating method, which is referred to as pinning, as a rule two to three Kirschner wires 9 introduced through holes will bridge the fracture and serve for its stabilization. By means of the fixating device according to the invention, the Kirschner wires 9 are retained in a positionally stable manner.

Figure 2:
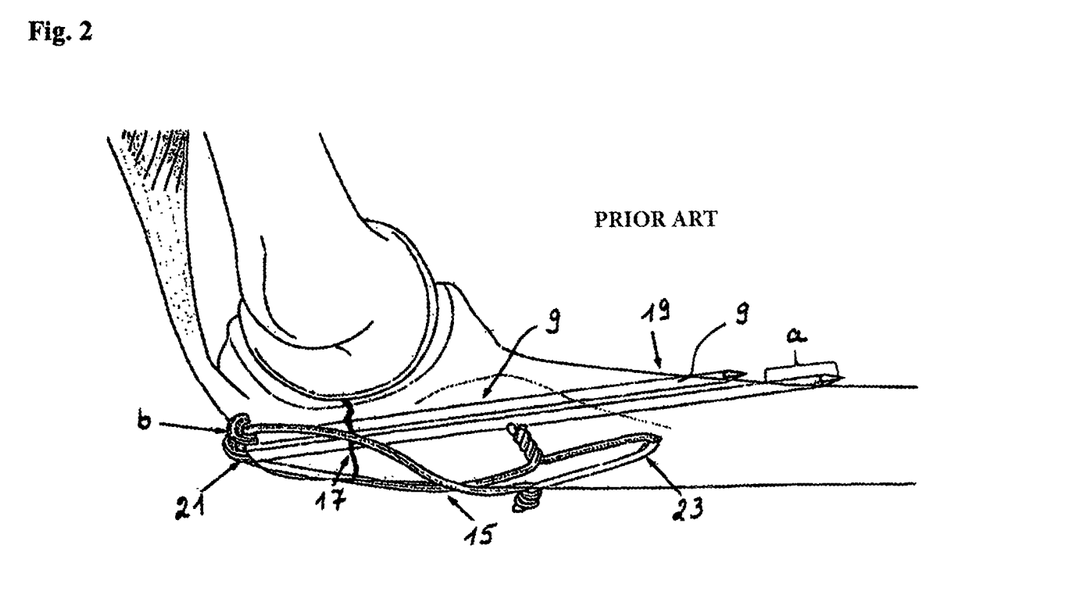
FIG. 2: a representation of the known principle of tensioning using the example of the olecranon according to the specifications of the Association for the Study of Internal Fixation.

A further application for the described fixating device 1 according to the invention is tension band wiring, which is explained in the following with reference to FIG. 2, using the example of the tension band wiring with the olecranon. Here, the presently known principle, and thus the known prior art, is presented:

For the application of the tension band wiring, the broken ends are brought together to a maximum and are first held by means of a clamp. In order not to allow the fracture gap indicated by the reference numeral 17 to be widened during stretching and to reduce shear forces, two Kirschner drill wires 9 are introduced parallel and longitudinally from one fragment through the fracture gap 17 to the other fragment, as close to the joint surface as possible. The aim is to also perforate the counter corticalis 19 and to leave the Kirschner drill wire 9 protruding less than 1 cm, which is indicated in FIG. 2 by the reference numeral a). A wire loop from a cerclage wire 15 is laid in an eight-shape around the ends 21 of the Kirschner drill wire 9 projecting from the bone in the proximity of the tendons, and is guided distally through a transversely extending bone bore 23. This results in an additional increase in stability. The drill wires 9 themselves are shortened, bent and also sunk in the bone, which has been made clear in FIG. 2 by the reference numeral b). This creates a further safeguard against backward loosening and traveling of the drill wires 9.

In the case of such tension band wiring, the fixating device according to the invention can do without an additional attachment to the bone, the tendons or other soft tissue structures.

In this application, it is also to be mentioned as an additional advantage of the above-described, overall domed configuration of the fixating device 1 according to the invention, that this results in a better covering of the tension band wiring at the point of intersection of the Kirschner wire 9 and the cerclage 15. The maximum load on the soft tissue lying above the bone fracture area is reduced by an increase in the surface.

EXEMPLARY EMBODIMENT I.2

Figure 3:
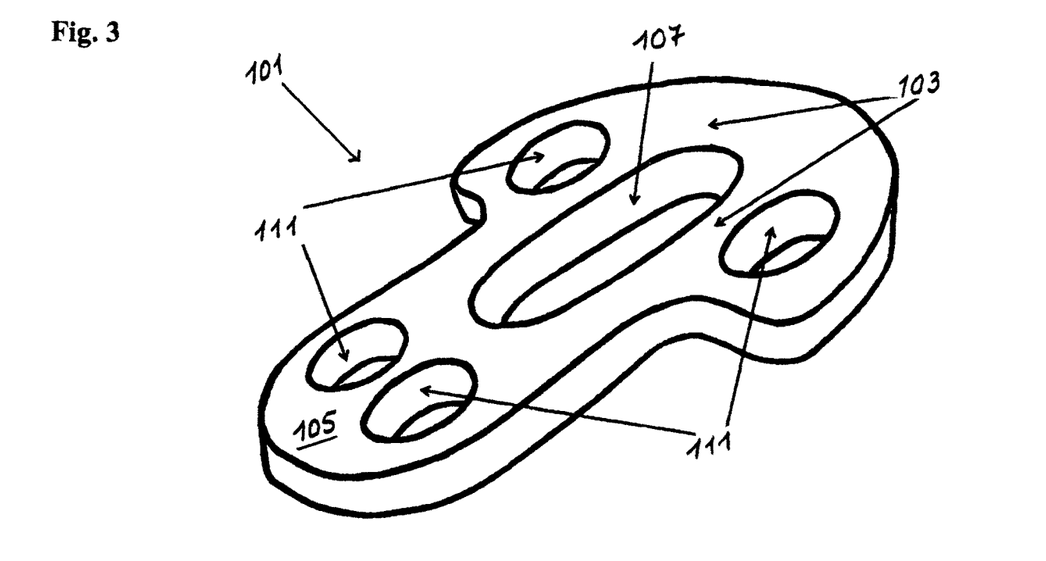
FIG. 3: a three-dimensional view of a fixating device according to the invention as a planar embodiment according to a variant of the first embodiment.

Fixating Device as Plate-Like Planar Design:

As a second embodiment, FIG. 3 shows a variant of the first embodiment of the fixating device according to the invention described under I.1, which is therefore only briefly explained below. To this end, for the first exemplary embodiment, identical features are provided with the same reference numerals, but expanded by 100.

The only difference to this variant of the fixating device 101 according to the invention is that it is not domed on all sides, but rather has a plate-like planar design. This has the advantage that the fixating device 101 can be adapted to the appropriate anatomical bone conditions by selecting in each case the convexity suitable for the appropriate medical treatment.

The fixating device 101 according to this variant of the first exemplary embodiment is also designed to have an approximately flattened, mushroom-shaped configuration, and has an enlarged head region 103 and a consequent taper 105. An opening designed as a longitudinal hole 107 is provided approximately centrally, which extends in the longitudinal direction thereof in the direction of the taper 105 of the fixating device 101, and whose narrow sides are closed by half-circles whose diameter corresponds to the width of the longitudinal hole 107. This longitudinal hole 107 serves to receive the bent-over part of a fastening means in the form of a drill wire or Kirschner wire, which is not illustrated here again. Reference is therefore made to the further explanations for the first exemplary embodiment. These apply analogously here. With regard to the diameter of the longitudinal hole 107 in its longitudinal direction, it is also important here that this longitudinal diameter is smaller than the maximum extent of the bent portion of the Kirschner wire 109 extending through the longitudinal hole 107 in this longitudinal direction.

In this variant of the first exemplary embodiment, in each case adjacently to the two ends in the longitudinal direction of the longitudinal hole 107, there are in each case two more openings designed as holes 111, which are formed circular. These serve to receive fastening material, as already explained.

The guidance of the cerclage wire is already illustrated in FIG. 1*b* in connection with the first embodiment, showing there, as already described, and here equally true, that the bent-over portion of the Kirschner wire 9 grips the cerclage wire 15. Also in this embodiment, the other holes 111 have a diameter of at least 0.6 mm in order to be able to incorporate strong fastening material.

In this variant of the fixating device 101 according to the invention of the first embodiment, the above-described advantages such as a significant improvement of the pressure conditions by reducing pressure on the overlying soft tissue, are also applicable. The maximum load of the soft tissue lying over the bone fracture region is reduced by an enlargement of the surface.

Suitable material for the fixating device 101 shown here is metal, preferably titanium. All edges of the respective openings of the fixating device, i.e., of the longitudinal hole 107, as well as the other, circular holes 111, are deburred. The same applies to the external edges of the fixating device.

The applications specified according to the first embodiment using only the Kirschner drill wire, without using the cerclage or the tension band wiring, are here just as possible, so that the configurations of the first embodiment II also apply and do not need to be repeated here.

When using the tension band wiring, the inventive fixating device of this variant with the convexity adapted to the corresponding anatomical bone conditions does not need additional attachment to the bones, tendons or other soft tissue structures, and in this way, again achieves better coverage of the tension band wiring at the intersection of the Kirschner wire and the cerclage.

EXEMPLARY EMBODIMENT I.3

Fixating Device as all-Round Domed Design or Plate-Like Planar Design with Reduced Hole Number The third embodiment of the fixating device according to the invention to be explained here is a variant of both the embodiment illustrated in I.1 as well as the variant described in I.2. This third embodiment is not further illustrated in the accompanying drawing.

The modification of the fixating device according to this third exemplary embodiment is again flattened in the plan and is approximately mushroom-shaped and has an enlarged head region, followed by a tapering. Approximately centrally, this fixating device has an opening designed as a longitudinal hole which extends in its longitudinal direction in the direction of the tapering of the fixating device and whose narrow sides are closed by half-circles whose diameter corresponds to the width of the longitudinal hole. This longitudinal hole also serves again to receive the bent part of a fastening means in the form of a drill wire or Kirschner wire, reference being made to FIGS. 1*b* and 1*c*. The bent part of the drill wire or Kirschner wire reaches through the longitudinal hole. The longitudinal and transverse diameters of the longitudinal hole depend on the strength of the Kirschner wire used and are matched to it, so that it cannot slip out of the longitudinal hole but remains fixated in it. For this purpose, the diameter of the longitudinal hole in its longitudinal direction is again made smaller than the maximum extent of the bent-over part of the Kirschner wire projecting through the longitudinal hole in this longitudinal direction.

The only difference between this variant and the two previous embodiments of the fixating device according to the invention is that in each case adjacent to the two ends, in the longitudinal direction of the longitudinal hole, there are no two additional openings designed as circularly formed holes which are provided for the fastening material, but instead, overall only three openings designed as these circularly formed holes.

These are arranged such on the fixating device that two of them are arranged at the end in the longitudinal direction of the longitudinal hole in the enlarged head region, while a single hole is provided at the end of the longitudinal hole in the region of the taper.

This advantageously results in a reduction in the diameter of the fixating device according to the invention, transversely to the orientation of the longitudinal hole.

EXEMPLARY EMBODIMENT II

Cap-Shaped Fixating Device as a Sphere Segment

Figure 4A:
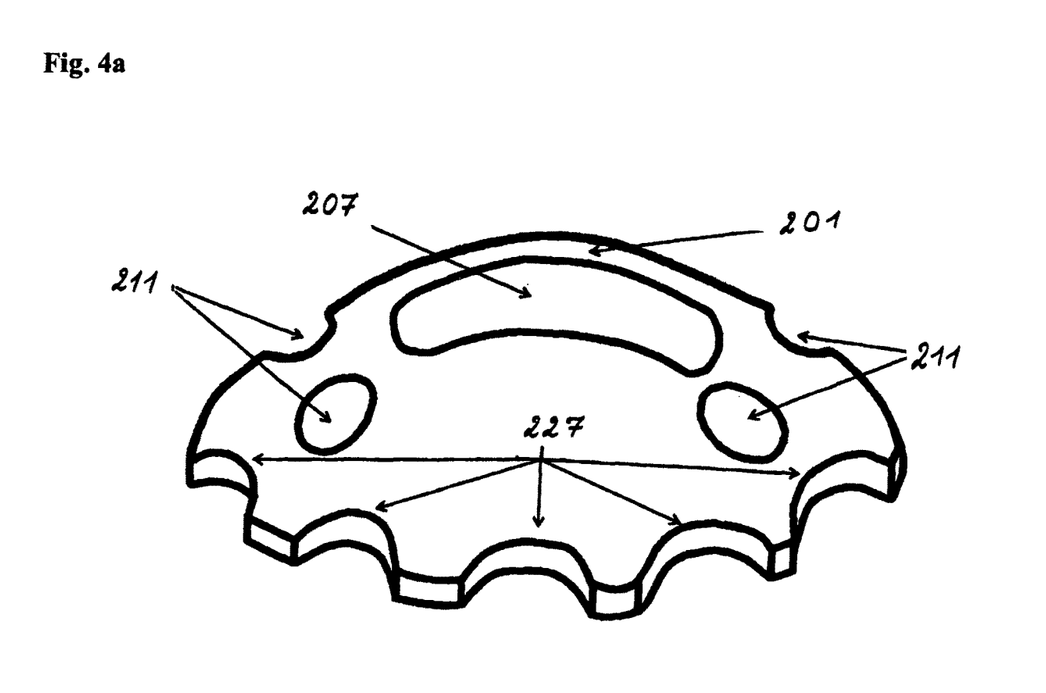
FIG. 4*a*: a three-dimensional view of a fixating device according to the invention according to a fourth embodiment designed as a cap, as a sphere segment.

FIG. 4a shows a fourth embodiment of the fixating device according to the invention, which is explained in the following. To this end, for the first exemplary embodiment, identical features are provided with the same reference numerals, but extended by 200.

Figure 4B:
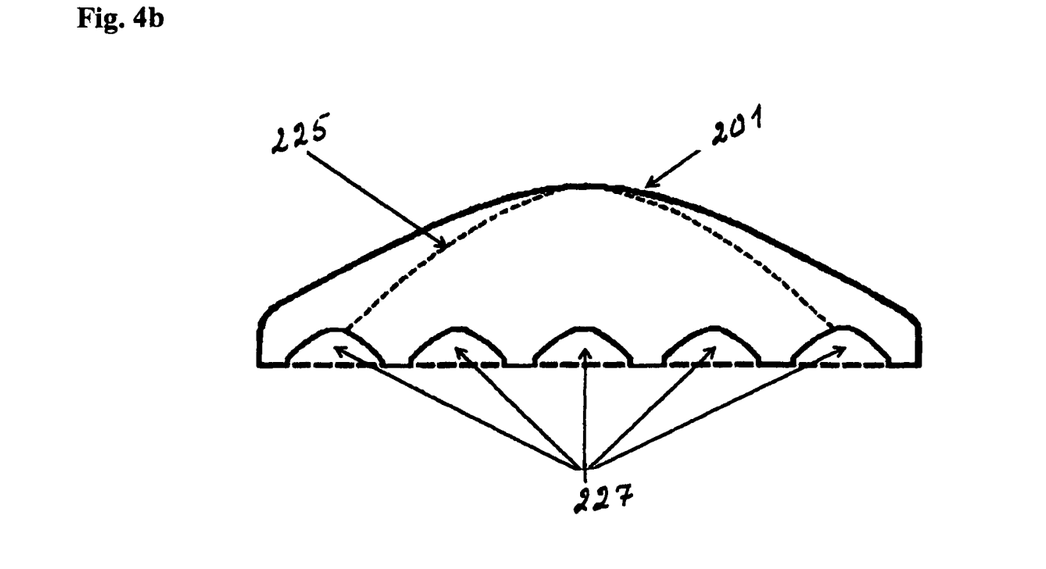
FIG. 4*b*: a cross-section of the fixating device according to FIG. 4*a*, in a schematic representation.

This embodiment of the fixating device 201 according to the invention is a cap, the cross-section of which corresponds, as shown in FIG. 4b, to a sphere segment. The fixating device 201 is bent in the manner of a cap or domed on all sides in such a way that the surface facing away from the bone to be fixated or from the body (distal to bone or body) is convex and the surface (proximate to bone or body) facing this bone or body is concave. Here again, a longitudinal hole 207 is located almost centrally. However, this is to be seen as an indentation in the fixating device 201 on the underside, which is indicated in FIG. 2b by the reference numeral 225. The longitudinal hole 207 also serves here to receive the bent-over part of the fastening means, not shown in detail in FIGS. 4a and 4b, in the form of a drill wire or Kirschner wire.

Proceeding from this longitudinal hole 207 are further radiating indentations 227 for receiving the cerclage wire, which are formed on the sphere segment. In this embodiment of the fixating device 201 according to the invention, too, further holes for accommodating the fastening material are incorporated and are provided with the reference numeral 211.

Suitable material for the illustrated fixating device 201, in addition to metal, here preferably titanium, is also plastic. All the edges of the respective openings of the fixating device, i.e., of the longitudinal hole 207 as well as the additional circular holes 211, are deburred in the exemplary embodiment. The same applies to the external edges of the fixating device.

EXEMPLARY EMBODIMENT III

Figure 5:
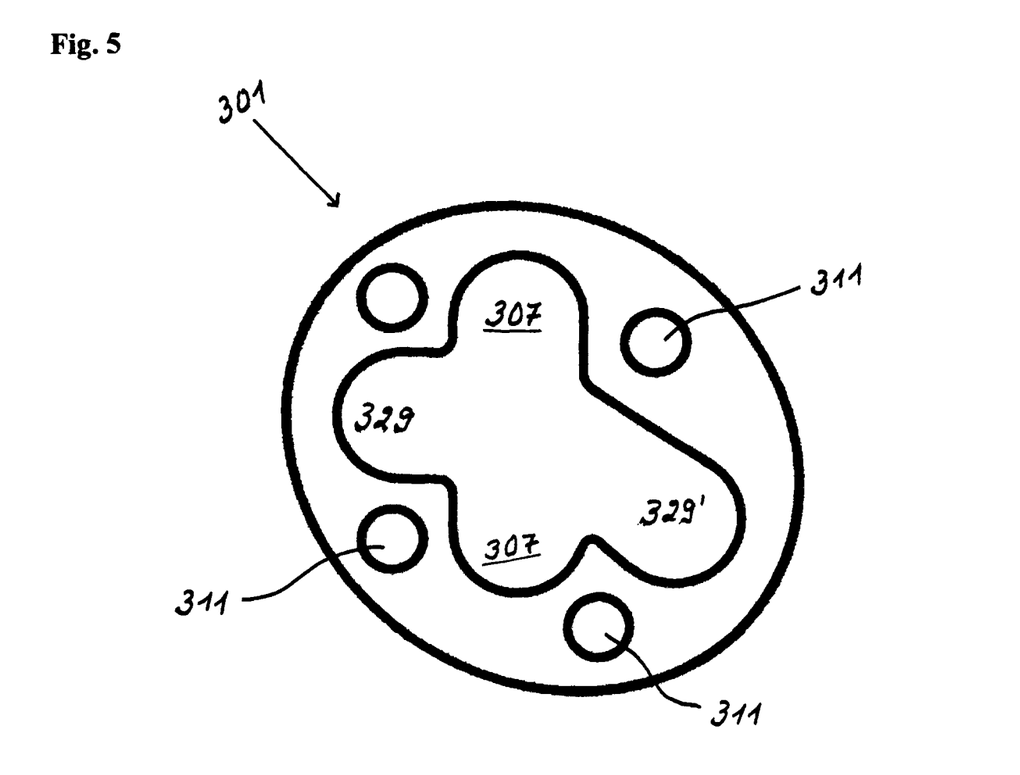
FIG. 5: a schematic plan view of a fixating device according to the invention, with an irregularly modified longitudinal hole.

Fixating Device with all-Round Domed Design or Plate-Like Planar Design and Modified Longitudinal Hole FIG. 5 shows a further embodiment of the fixating device according to the invention. For purposes of explanation, the same features are provided with the same reference numerals as for the first exemplary embodiment, but extended by 300.

This embodiment is shown in a two-dimensional view, as shown in FIG. 5. This makes it clear that it can be domed on all sides as well as in a plate-like planar design. For the embodiment in plate-like planar form, it has already been explained above that this has the advantage of being able to adapt the fixating device 301 to the corresponding anatomical bone conditions by selecting the suitable convexity appropriate for medical treatment.

These explanations are also intended to apply generally to the further embodiments to be explained hereinafter.

The fixating device 301 according to this exemplary embodiment is designed approximately oval in plan, but can also be circular in plan.

Arranged approximately centrally in this oval, the fixating device 301 has an opening designed as a modified longitudinal hole 307. This longitudinal hole 307 has a respective bulge 329, 329' on both sides along its longitudinal direction, which are irregularly molded relative to one another, in this exemplary embodiment. In this case too, the longitudinal hole 307 serves to receive the bent-over part of a fastening means in the form of a drill wire or Kirschner wire, not shown in detail in FIG. 5, with the bent part of the drill wire or Kirschner wire reaching through the longitudinal hole 307.

With reference to the first exemplary embodiment, it has been pointed out in I.1 that the longitudinal and transverse diameters of the longitudinal hole 307 are based on and matched to the strength or thickness of the Kirschner wire used. The longitudinal and transverse diameters of the longitudinal hole 307 thus vary depending on the strength of the Kirschner wire to be used. The transverse diameter of the longitudinal hole 307, which according to the first exemplary embodiment is designed such that it corresponds to the diameter of the Kirschner wire used plus at least 0.05 mm, preferably plus 0.1 mm, and at most plus 1.0 mm, is essential.

With respect to the diameter of the longitudinal hole 307 in its longitudinal direction, it is important that this longitudinal diameter is configured smaller than the maximum extent of the bent part of the Kirschner wire projecting through the longitudinal hole 307 in this longitudinal direction.

With the configuration of the longitudinal hole 307 according to the embodiment described here, a greater degree of freedom is achieved in the medical treatment of a bone fracture. Because the bulges 329, 329' are formed on both sides along the longitudinal direction of the longitudinal hole 307, and particularly because they are irregularly molded and oriented relative to one another, the fixating device 301 provides a recess for the cerclage wire in the sense that the fixating device 301 is better able to mold to the corresponding bone fracture during medical treatment and does not protrude through the guide of the cerclage wire coming from below.

In each case, two further openings are provided designed as holes 311, each of which is circular in shape, adjacent to the bulges 329, 329' or to the two ends oriented in the longitudinal direction of the longitudinal hole 307. These are used to receive fastening material. This has already been explained further above under I.1 with regard to the first exemplary embodiment.

The fixating device 301 is bent or domed on all sides. If appropriate, proceeding from the plate-like planar design, it is adapted to the corresponding anatomical bone conditions by selecting the suitable convexity appropriate for medical treatment. In this case, the surface (distal to the body) facing away from the imaginary body which is to be fixated is convex, and the surface (proximate to the body) facing this body is concave. The advantages of this curvature have already been pointed out.

Suitable material for the illustrated fixating device 301 in the bent or all-round domed configuration is metal, here preferably titanium, and plastic. In the case of the initially plate-like planar design, which is then matched to the corresponding anatomical bone conditions by selecting the suitable convexity appropriate for medical treatment, metal and plastic are also suitable as material.

All the edges of the respective openings of the fixating device 301, i.e., of the longitudinal hole 307, of the bulges 329, 329' as well as of the additional circularly shaped holes 311, are deburred in the exemplary embodiment. The same applies to the external edges of the fixating device.

As with all previous embodiments of the fixating device according to the invention, this embodiment can also be used with the sole application of one or more Kirschner drill wires and in connection with cerclage in the case of tensioning. By means of the fixating device according to the invention, the Kirschner wires are retained in a positionally stable manner.

EXEMPLARY EMBODIMENT IV.1-IV.3

Figure 6A:
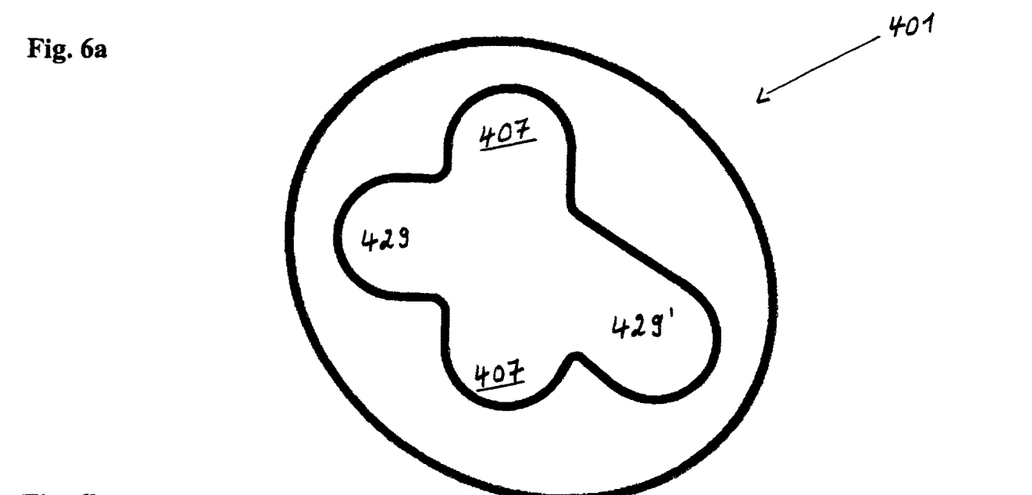
FIG. 6*a*: a schematic plan view of a fixating device according to the invention with an irregularly modified longitudinal hole as the sole opening.
Figure 6B:
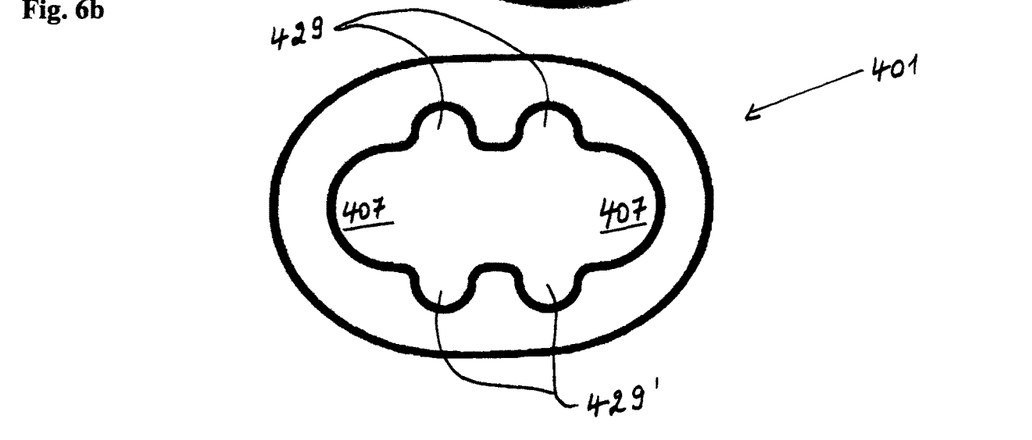
FIG. 6*b*: a schematic plan view of a fixating device according to the invention with an oval ground plan and a longitudinal hole as the sole opening, modified in each case with two bulges formed on both sides.
Figure 6C:
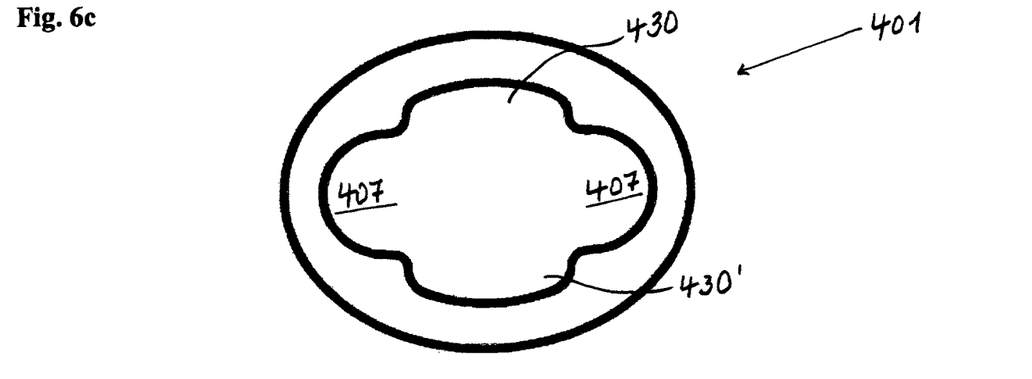
FIG. 6*c*: a schematic plan view of a fixating device according to the invention with an oval contour and a longitudinal hole as the sole opening according to FIG. 6*b*, wherein the two bulges, which are provided on both sides to the longitudinal hole, are each fused into a single bulge.

Fixating Device in all-Round Domed Design or Plate-Like Planar Design with Modified Longitudinal Hole as the Sole Opening FIGS. 6a-6c show further embodiments of the fixating device according to the invention in a combined manner, and, for their explanation, the same features as those of the first exemplary embodiment, but with the reference numerals extended by 400, are provided.

All representations of FIGS. 6a-6c are shown in a two-dimensional view. They can be domed on all sides as well as a n plate-like planar design. The plate-like planar design can again be adapted to the corresponding anatomical bone conditions by selecting the suitable convexity appropriate for medical treatment.

The fixating device 401 according to the variants of this exemplary embodiment shown in FIGS. 6a and 6b is each designed approximately oval in plan. Arranged approximately centrally in this oval, the respective fixating device 401 has an opening designed as a modified longitudinal hole 407.

The fixating device 401 according to the variant shown in FIG. 6a corresponds in this respect to the embodiment according to Example III in that the longitudinal hole 407 has in each case a bulge 429, 429', which are irregularly molded relative to one another, on both sides along its longitudinal direction.

In the case of the fixating device 401 according to the variant shown in FIG. 6b, the longitudinal hole 407 has two bulges 429, 429' on both sides along its longitudinal direction, which are regularly molded relative to one another. A further variant, which is not shown separately, consists in the fact that the fixating device 401, according to the variant illustrated in FIG. 6b, is, however, approximately circular in plan.

In the case of the fixating device 401 according to the variant of this exemplary embodiment illustrated in FIG. 6c, the bulges of the embodiment arranged in pairs, as shown in FIG. 6b, respectively merge into a single bulge provided with the reference numerals 430, 430'. As a result, the indent formed between them according to the variant illustrated in FIG. 6b, disappears. In all three variants, the longitudinal hole 407 serves to receive the bent-over part of a fastening means in the form of a drill wire or Kirschner wire not further shown in FIGS. 6a-6c, and the bent part of the drill wire or Kirschner wire reaches through the longitudinal hole 407 without slipping through it. For this purpose, the diameter of the longitudinal hole 407 in its longitudinal direction is again made smaller than the maximum extent of the bent part of the Kirschner wire projecting through the longitudinal hole 407 in this longitudinal direction.

In contrast to the embodiments described thus far, in the case of the three variants, as illustrated in FIGS. 6a-6c, no further openings are provided for receiving further fastening material, in addition to the one opening designed as the longitudinal hole 407.

As a result, these embodiments distinguish themselves for use in small or smaller bones and represent variants which also enable simplified manufacture.

All the variants described are either domed on all sides or arched from the outset, or have a plate-like planar design, which can again be adapted to the corresponding anatomical bone conditions by selecting the suitable convexity appropriate for medical treatment.

In this case, the surface (distal to the body) facing away from the imaginary body to be fixated is convex, and the surface (proximate to the body) facing this body is concave. The advantages of this curvature have already been pointed out.

Suitable materials for these variants of the fixating device 401 according to the invention in the case of the different embodiments mentioned are metal, in this case preferably titanium, and plastic.

All the edges of the respective openings of the fixating device 401, i.e. of the longitudinal hole 407 and of the bulges 429, 429' are deburred in the exemplary embodiment. The same applies to the external edges of the fixating device.

As with all previous embodiments of the fixating device according to the invention, this embodiment can also be used with the sole application of one or more Kirschner drill wires in connection with the cerclage in the case of tensioning. By means of the fixating device according to the invention, the Kirschner wires are retained in a positionally stable manner.

EXEMPLARY EMBODIMENTS V.1 AND V.2

Fixating Device in All-Round Domed Design or Plate-Like Planar Design, Designed as an Annular Oval FIGS. 7a and 7b once again show further embodiments of the fixating device according to the invention in a combined manner, and, for the purpose of explaining the same, the same features as in the first exemplary embodiment are designated with the same reference numerals, but extended by 500.

Figure 7A:
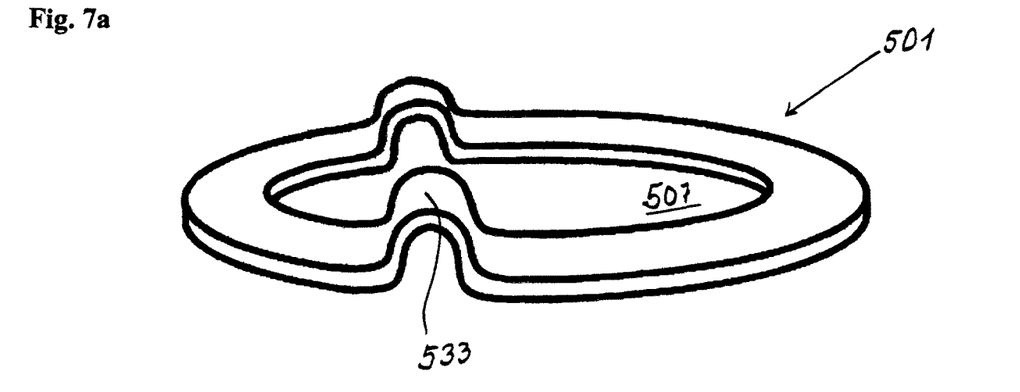
FIG. 7*a*: a schematic side view of a fixating device according to the invention designed as an annular oval with a lateral tunnel-like elevation.
Figure 7B:
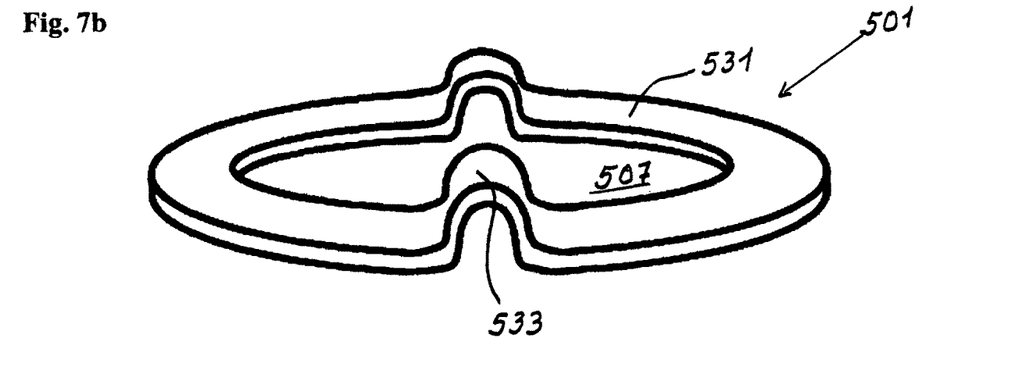
FIG. 7*b*: a schematic side view of a fixating device according to the invention designed as an annular oval with an approximately central tunnel-like elevation.

The representations of FIGS. 7a and 7b correspond to a two-dimensional view. The embodiments can be domed on all sides as well as in a plate-like planar design. The plate-like planar design can be adapted to the corresponding anatomical bone conditions by selecting the suitable convexity for the appropriate medical treatment. The (distal to the body) surface facing away from the imaginary body to be fixated is convex, and the surface (proximate to the body) facing this body is concave. The advantages of this curvature have already been mentioned.

In the case of these two variants of fixating devices 501 as shown in FIGS. 7a and 7b, no further opening for receiving further fastening material is provided in addition to the one opening designed as the longitudinal hole 507.

The fixating device 501 according to the variants shown in FIGS. 7a and 7b of this exemplary embodiment is designed approximately oval in plan. In each of these variants, an annular oval 531 is formed, which in its interior defines an opening designed as an oval longitudinal hole 507. The longitudinal hole 507 receives the bent-over part of a fastening means in the form of a drill or Kirschner wire, not shown in detail in FIGS. 7a and 7b, and the bent part of the drill wire or Kirschner wire reaches through the oval longitudinal hole 507 in the manner already described.

In the variants shown in FIGS. 7a and 7b, tunnel-like elevations 533 are arranged on the said annular oval 531 opposite one another and cooperating with each other. 7a and 7b thereby differ in that in FIG. 7a, the above-mentioned tunnel-like elevations 533 are offset from the center of the annular oval 527, whereas they are centered according to the variant shown in FIG. 7b.

The fastening material in the form of stitches or wires can now be passed through the above-mentioned tunnel-like elevations 533 without shearing them off. The mutually corresponding tunnel-like elevations 533 allow for the fixating device 501 to better mold to the corresponding bone fracture during medical treatment and to not protrude through the guide of the cerclage wire coming from below.

Suitable materials for these variants of the fixating device 501 according to the invention in the case of the different embodiments described are metal, in this case preferably titanium, and plastic.

All the edges of the respective openings of the fixating device 501, i.e. of the longitudinal hole 507 and the tunnel-like elevations 533, are deburred in the exemplary embodiment. The same applies to the outer edges of the fixating device 501.

As with all previous embodiments of the fixating device according to the invention, this embodiment can also be used with the sole application of one or more Kirschner drill wires and in connection with the cerclage in the case of tensioning. By means of the fixating device according to the invention, the Kirschner wires are retained in a positionally stable manner.

EXEMPLARY EMBODIMENTS VI.1-VI.4

Fixating Device in All-Round Domed Design or Plate-Like Planar Design with a Single Opening and in Reduced Form FIGS. 8a to 8d show embodiments of the fixating device according to the invention which have the same features as those of the first exemplary embodiment, with the same reference numerals, but which are extended by 600. The representations correspond to a two-dimensional view. The embodiments can be domed on all sides as well as in a plate-like planar design. The (distal to the body) surface facing away from the imaginary body to be fixated is convex, and the surface (proximate to the body) facing this body is concave. The advantages of this curvature have already been mentioned.

In the illustrated variants of FIGS. 8a-8d, no further opening or other guide is provided for receiving further fastening material in the form of stitches or wires in addition to the one opening designed as the longitudinal hole 607.

Figure 8A:
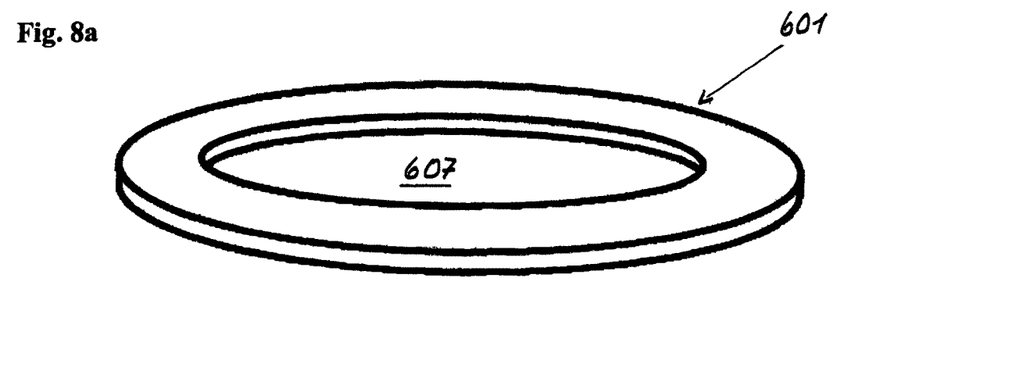
FIG. 8*a*: a schematic side view of a fixating device according to the invention designed as an annular oval.
Figure 8B:
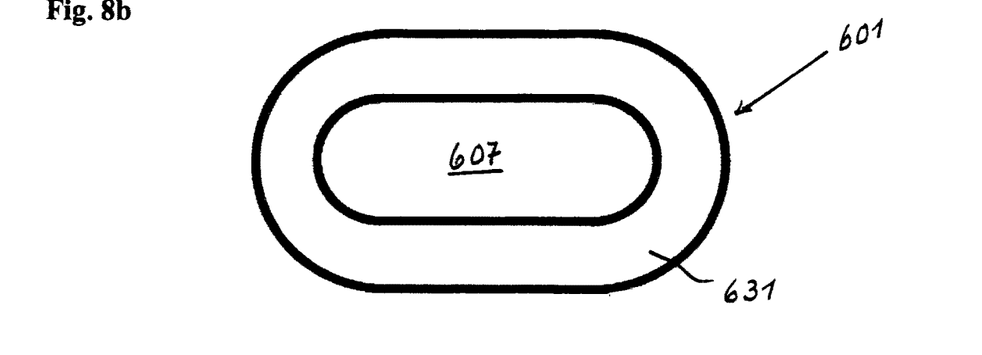
FIG. 8*b*: a schematic plan view of the fixating device designed as the annular oval according to FIG. 8*a*, FIG. 8*c*: a schematic plan view of a fixating device according to the invention, with a circular contour and an opening designed as an oval longitudinal hole.
Figure 8C:
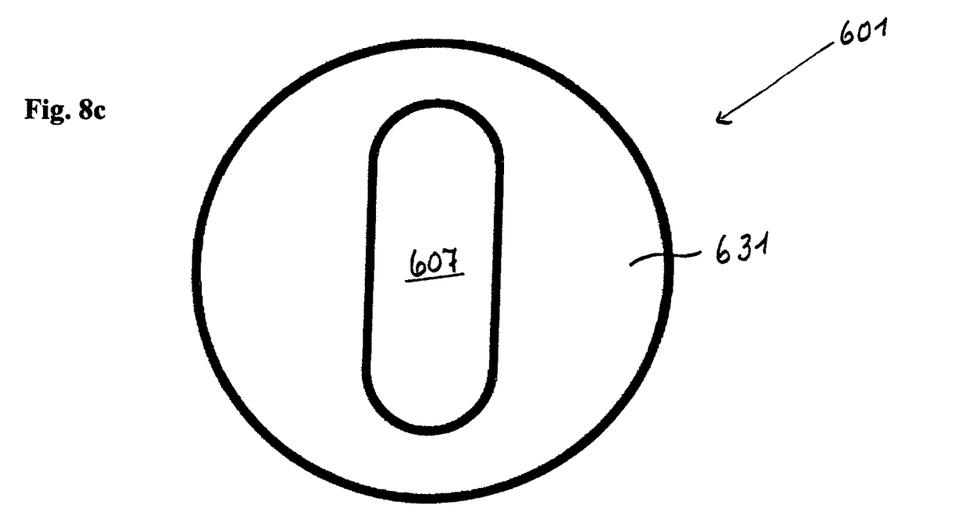

The fixating device 601 according to the variant of this exemplary embodiment shown in FIG. 8a is formed in plan approximately as an annular oval 631, which in this way defines an opening designed as an oval longitudinal hole 607 in its interior. FIG. 8b shows this again as a plan view. The fixating device 601 according to the variant shown in FIG. 8c, on the other hand, has a circular contour, with an opening designed as an oval longitudinal hole 607.

Figure 8D:
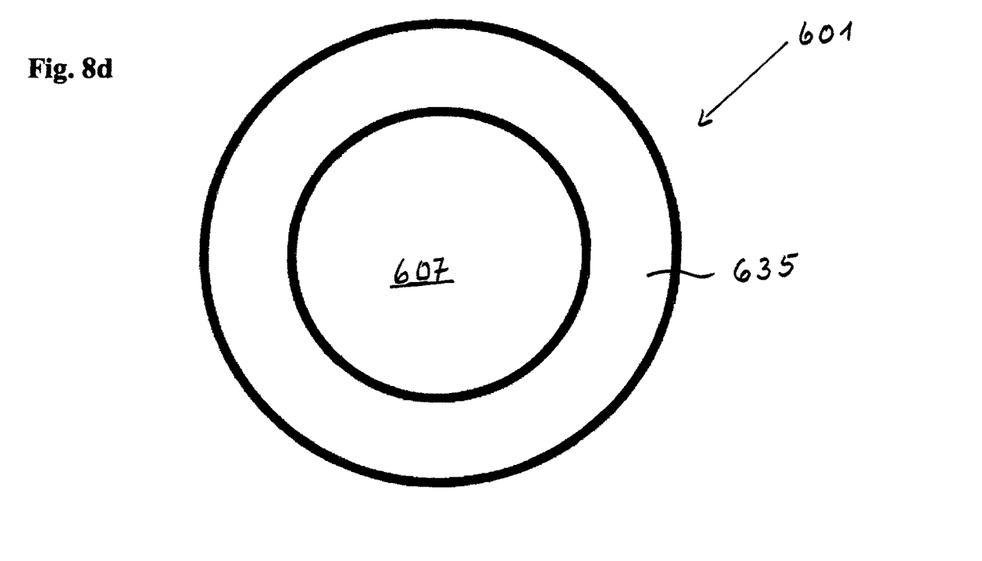
FIG. 8*d*: a schematic plan view of a fixating device according to the invention designed as a circular ring with an opening designed as a round hole.

The fixating device 601 according to the variant of this exemplary embodiment shown in FIG. 8d is designed overall as a circular ring 635 with an opening designed as a round hole 607 in its interior.

In these variants too, the longitudinal hole 607 receives the bent-over part of a fastening means in the form of a drill wire or Kirschner wire which is not shown in more detail in FIGS. 8a to 8d, and the bent part of the drill wire or Kirschner wire reaches through the respective longitudinal hole 607 in the already described manner, i.e., in particular, with the drill wire or Kirschner wire being retained in the longitudinal hole without slipping through it. For this purpose, the diameter of the longitudinal hole 607 in its longitudinal direction is again made smaller than the maximum extent of the bent part of the Kirschner wire projecting through the longitudinal hole 607 in this longitudinal direction.

These embodiment variants are for use with small or smaller bones and are manufactured of metal, here preferably titanium, and plastic. All the edges of the respective openings of the fixating device 601 are deburred. The same applies to the external edges of the fixating device 601.

The invention claimed is:

1. A fixating device and a fastener for use in surgery, the fixating device cooperating with the fastener and a fastening material, the fixating device comprising:
   at least one opening for receiving the fastener, the fastener reaching through the at least one opening and being retained in a positionally stable manner by the at least one opening and by the fastening material,
   wherein the at least one opening is a longitudinal hole, the longitudinal hole being a through-hole that extends through a top surface and a bottom surface of the fixating device, and the longitudinal hole having a major axis and a minor axis, and
   wherein a length of the at least one opening along the major axis is smaller than a maximum width of a bent, U-shaped portion of the fastener, such that during insertion of the bent, U-shaped portion of the fastener through the at least one opening, the bent, U-shaped portion of the fastener will become wedged within the at least one opening.

2. The fixating device according to claim 1, wherein the fixating device is a planar plate, or is domed on all sides or is provisioned in the shape of a cap as a sphere segment.

3. The fixating device according to claim 1, wherein the fixating device comprises, in addition to the at least one opening, at least two further openings for receiving the fastening material.

4. The fixating device according to claim 1, wherein the fixating device has an enlarged head region adjoined to a tapered region.

5. The fixating device according to claim 4, wherein the longitudinal hole extends from the enlarged head region into the tapered region.

6. The fixating device according to claim 5, further comprising four openings to receive the fastening material, wherein two of the four openings are provided in the enlarged head region on opposing sides of the longitudinal hole, and the other two of the four openings are provided in the tapered region.

7. The fixating device according to claim 6, wherein the other two of the four openings, that are provided in the tapered region, are positioned directly adjacent to each other.

8. The fixating device according to claim 1,
   wherein the longitudinal hole has at least two bulges,
      wherein the at least two bulges are regularly or irregularly molded on the longitudinal hole relative to one another.

9. The fixating device according to claim 1, wherein the fixating device is designed as a sphere segment, with indentations distributed on a periphery of an outer boundary of the sphere segment.

10. The fixating device according to claim 1, wherein the fixating device has an annular oval shape, with the longitudinal hole in an interior of the annular oval shape, wherein tunnel-like elevations are arranged on the annular oval shape opposing one another and cooperating with each other.

11. The fixating device according to claim 1, wherein the fastener is a Kirschner wire or a drill wire.

12. The fixating device according to claim 1, wherein the fastener is a Kirschner wire or a drill wire, wherein the minor axis of the longitudinal hole is made to accommodate a diameter of the Kirschner wire or the drill wire.

13. The fixating device according to claim 12, wherein the minor axis of the longitudinal hole corresponds to the diameter of the Kirschner wire or the drill wire, plus 0.05 mm to 1.0 mm.

14. The fixating device according to claim 13, wherein the fastening material is stitches or wires.

15. The fixating device according to claim 1, wherein the fixating device is made of plastic or metal, wherein the metal is selected from stainless steel or titanium.

16. The fixating device according to claim 1, wherein the fixating device is a planar plate, such that an entirety of the fixating device extends on a single plane.

17. The fixating device according to claim 1, wherein an entire perimeter of the longitudinal hole extends through the top surface and the bottom surface of the fixating device.

\* \* \* \* \*